United States Patent [19]

Brucker

[11] Patent Number: 5,223,229
[45] Date of Patent: Jun. 29, 1993

[54] STERILIZING APPARATUS HAVING AUTOMATICALLY ACTUATED DOOR

[75] Inventor: Jeffrey P. Brucker, Troy, Ohio

[73] Assignee: Midmark Corporation, Versailles, Ohio

[21] Appl. No.: 554,659

[22] Filed: Jul. 19, 1990

[51] Int. Cl.$^5$ .................................. A61L 2/24
[52] U.S. Cl. .................... 422/116; 422/112; 422/295; 422/298; 49/395; 292/36
[58] Field of Search .............. 422/26, 295, 298, 116, 422/112; 292/32, 33, 36; 49/394, 395

[56] References Cited

U.S. PATENT DOCUMENTS

| | | |
|---|---|---|
| 2,613,130 | 10/1952 | Jewell et al. |
| 3,087,210 | 4/1963 | Neiss |
| 3,298,776 | 1/1967 | Beecher |
| 3,351,422 | 11/1967 | Jones et al. |
| 3,385,655 | 5/1968 | Huston et al. |
| 3,431,065 | 3/1969 | Schipanski ............... 422/298 X |
| 3,826,612 | 7/1974 | Black ..................... 422/298 X |
| 4,261,950 | 4/1981 | Bainbridge et al. ........... 422/26 |
| 4,426,358 | 1/1984 | Johansson .................. 49/394 X |
| 4,848,031 | 7/1989 | Yamagishi et al. ........... 49/394 X |
| 4,951,693 | 8/1990 | Archambault ............... 134/57 |

*Primary Examiner*—James C. Housel
*Assistant Examiner*—Jeffrey R. Snay
*Attorney, Agent, or Firm*—Biebel & French

[57] ABSTRACT

A sterilizer is disclosed which includes control circuitry for automatically controlling a plurality of sterilization cycles. The control circuitry operates to control actuation of a door opening mechanism whereby a door of the sterilizer may be automatically opened a small amount at the conclusion of a sterilization cycle whereby the sterilizer may initiate a drying portion of the cycle without the assistance of an operator. In addition, a baffled water reservoir is provided such that a water filling area of the reservoir is separated from a steam recovery area of the reservoir to thereby provide efficient recovery of steam at the conclusion of a sterilization cycle.

26 Claims, 9 Drawing Sheets

STERILIZING APPARATUS HAVING AUTOMATICALLY ACTUATED DOOR

BACKGROUND OF THE INVENTION

The present invention relates generally to sterilizers and, more particularly, to a sterilizer having control means for automatically controlling a sterilization process.

Sterilizers are widely used to sterilize articles in medical environments and typically employ a steam filled chamber for containing the article and means for increasing the temperature and pressure inside the chamber to a point where the article is sterilized.

Sterilizers may be used to sterilize either solid or liquid articles and, in a typical sterilization cycle for solid articles, the articles are sealed within a chamber of the sterilizer and steam may be supplied to the chamber. The steam may either be provided by means of a separate steam producing chamber or by supplying water to the chamber and heating the chamber until the water evaporates. In either case, the chamber is provided with a heater to elevate the temperature in the chamber and cause an accompanying increase in pressure such that sterilization of the articles is effected. Further, the presence of steam in the chamber facilitates an increase in pressure therein whereby the temperature and time required for completing the sterilization process may be kept to a minimum.

At the conclusion of the sterilization cycle, the steam in the chamber may be exhausted to a water reservoir where the steam is condensed for reuse in a subsequent cycle. The sterilizer disclosed in U.S. Pat. No. 3,351,422 to Jones et al is typical of such a sterilizer design and includes conduits for conveying water from a reservoir to a sterilization chamber and for conveying steam formed in the chamber back to the reservoir. The reservoir of the Jones et al patent has an open top which allows access to view the water level in the reservoir and to fill the reservoir when necessary. Such an arrangement is subject to a certain amount of evaporation and loss of water from the sterilizer system as steam condenses and exits from the condensing coil and comes into contact with the air above the reservoir water.

Personnel operating the sterilizer typically release additional steam from the sterilizer chamber by opening the sterilizer door after the pressure within the chamber has been reduced to a level near atmospheric pressure and before the articles in the chamber have cooled, such that any moisture remaining on the articles is caused to evaporate more quickly as the moisture content of the chamber decreases. By including this step in the sterilization cycle, the time required for the chamber and the article contained therein to reach a reduced temperature is decreased. Further the elevated temperature of the articles at the time when the door is opened insures that the articles will be completely dry when they are cool enough to be removed from the chamber.

The above cooling and drying step of the sterilization cycle is typically facilitated by a timer which sounds an audible warning signal when the pressure in the chamber has reached a safe level for the door to be opened. Obviously, this step requires that a person be in attendance near the chamber as the sterilization cycle is nearing completion in order for the chamber to be opened prior to the temperature of the articles decreasing to a point where the moisture will no longer evaporate from them. The door opening step may only be completed after the pressure within the chamber has been significantly reduced to avoid the possibility of the pressurized gases within the chamber causing the door to spring open and strike the operator.

Accordingly, there is a need for a sterilizing apparatus which may be operated automatically with a minimum of supervision from operating personnel and which incorporates a door opening step in its sterilization cycles. Further, there is a need for a sterilizing apparatus which automatically opens its door a controlled amount at the conclusion of sterilization cycles.

In addition, there is a need for a sterilizing apparatus which efficiently controls the recovery of steam within the water reservoir such that a minimum of steam is lost during the sterilization cycles.

SUMMARY OF THE INVENTION

The present invention provides a sterilizer for sterilizing solid and liquid articles in a steam environment at above atmospheric pressures and at preselected temperatures.

The sterilizer of the present invention includes a sterilizing chamber having means defining a chamber opening at a front portion of the chamber and through which articles may be placed into the chamber. A heating element is located along a lower portion of the chamber whereby water located in the chamber may be heated to form steam during a sterilization cycle.

A door is mounted adjacent to the front portion of the chamber and is movable from a closed position in engagement with the chamber to close off the chamber opening and an open position spaced from the chamber for insertion of articles into the chamber. The door is held in position adjacent to the chamber opening by catch and latch means mounted in stationary relationship to the chamber and door, respectively.

The catch means includes a pair of vertically spaced rails which define horizontal surfaces extending away from the front portion of the chamber. Each of the horizontal surfaces have means defining an aperture therein to form a first stop for the latch means, and means defining a vertical surface extending from each of the horizontal surfaces and facing toward the first stop to form a second stop for the latch means.

The latch means include a pair of vertically spaced pins and a vertically extending connecting member which connects the pins. In addition, a latch bracket is mounted between the pins and defines a horizontal surface extending from the connecting member. The connecting member, latch bracket and pins are vertically movable relative to the door and the catch means such that the pins may move into the apertures forming the first stop to hold the door in engagement over the chamber opening. Further, the pins may move out of the apertures to allow the door to pivot to a position intermediate the opened and closed positions wherein the pins engage the second stop to permit gasses to escape from the chamber between the door and the chamber opening.

Release means are provided for causing the latch means to disengage from the first stop means. The release means includes a bar extending toward the door from a point adjacent to the chamber and is mounted for movement about a horizontal axis. A forward end of the bar is located for engaging the horizontal surface of the latch bracket when the door is in its closed position, and a solenoid actuated plunger is provided for causing the bar to pivot about its horizontal axis whereby the connecting member is moved vertically relative to the door. As the connecting member is moved vertically, the pins are caused to disengage from the first stop such that gas within the chamber may exert pressure on the door to move the pins into engagement with the second stop. Thus, the door may be automatically opened to facilitate the drying of articles at the conclusion of a sterilization cycle, as moisture is allowed to escape past the chamber door.

The sterilizer further includes a reservoir for containing water and which has a front end adjacent to the front portion of the chamber. A window is located in the front end whereby the water level in the reservoir may be viewed. In addition, baffle means are formed in the reservoir for separating the reservoir into front and rear portions wherein the front portion includes a fill spout for filling the reservoir with water.

The rear portion of the reservoir forms a condensing cell for receiving and condensing steam from the chamber. The reservoir baffle extends from an uppermost portion of the reservoir downwardly to a point below a predetermined minimum level for water in the reservoir, such that the baffle and water in the reservoir together form a vapor barrier between the front and rear portions and thereby prevent steam from exiting from the reservoir through the front portion. A condensing coil located in the condensing cell receives steam from the chamber and is substantially located below the predetermined minimum water level. Steam from the chamber enters the coil below the minimum water level and exits the coil at a point above the minimum water level such that the steam in the coil travels upwardly as it is condensed.

Control means are provided for controlling the sequence of steps in the sterilization processes and includes a conventional microprocessor for receiving and processing inputs from sensors which monitor the temperature and pressure within the chamber as well as sensors for registering the water levels in the reservoir and chamber and for sensing when the door is in its closed position. The control means controls flow of water to the chamber and flow of steam back to the reservoir as well as controls the supply of power to the heating element for regulating the temperature within the chamber. The control means further actuates the solenoid actuated plunger of the release means to cause the sterilizer door to partially open at the conclusion of a sterilization cycle.

Thus, the sterilizer of the present invention provides a particular advantage over the prior art sterilizers in that the chamber door may be automatically actuated to insure that the moisture within the chamber is released such that the articles may undergo a drying stage at the conclusion of a sterilization cycle.

Further, the sterilizer of the present invention provides a unique water reservoir for insuring that steam which is returned to the reservoir from the chamber is condensed within the reservoir and not allowed to escape through the reservoir fill spout. In addition, the window on the front of the reservoir provides an easily accessible means for directly determining the water level within the reservoir.

Other objects and advantages of the invention will be apparent from the following description, the accompanying drawings and the appended claims.

DETAILED DESCRIPTION OF THE PREFERRED EMBODIMENT

Figure 1:
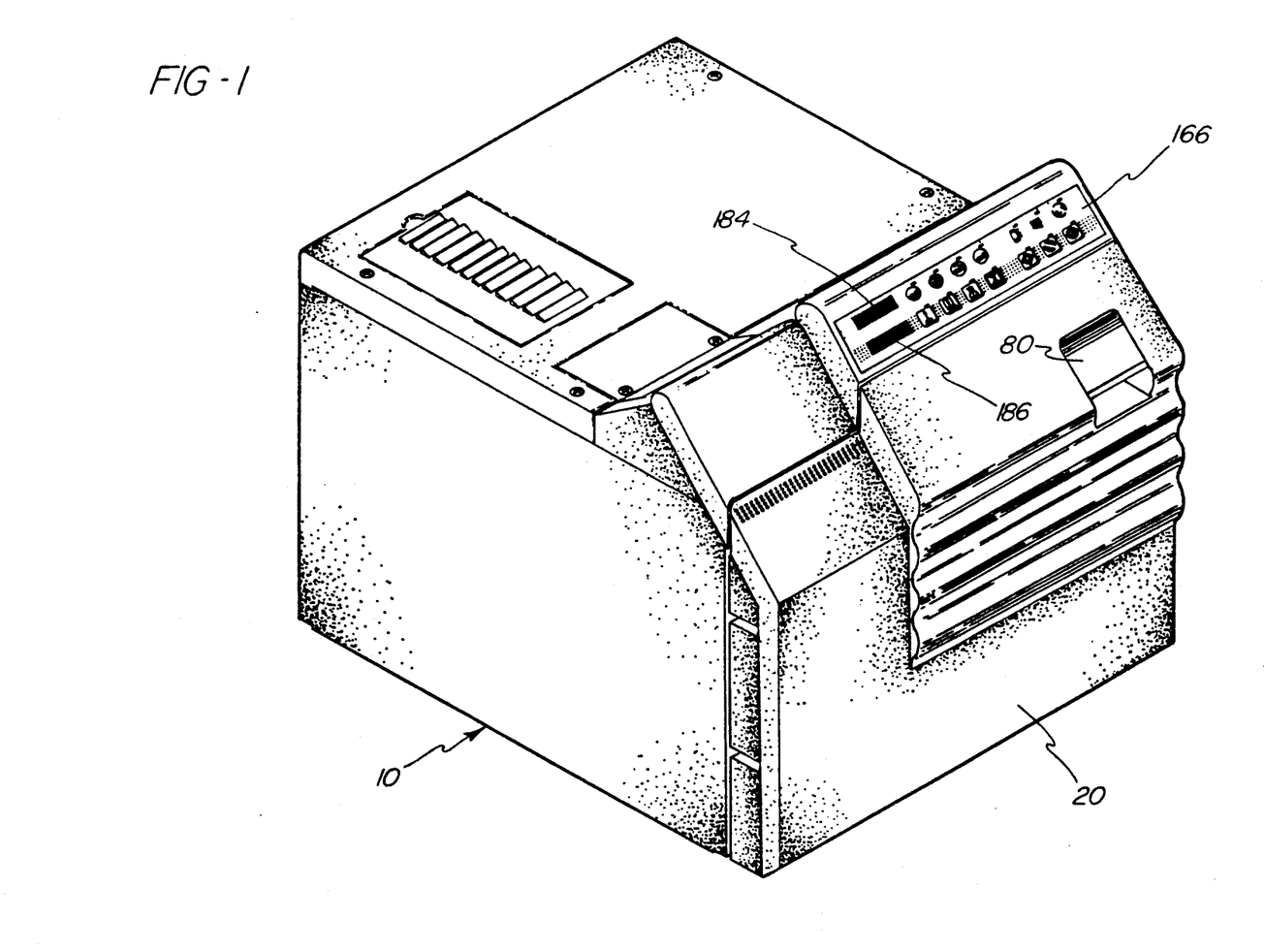
FIG. 1 is a perspective view of the exterior of the sterilizer of the present invention.
Figure 2:
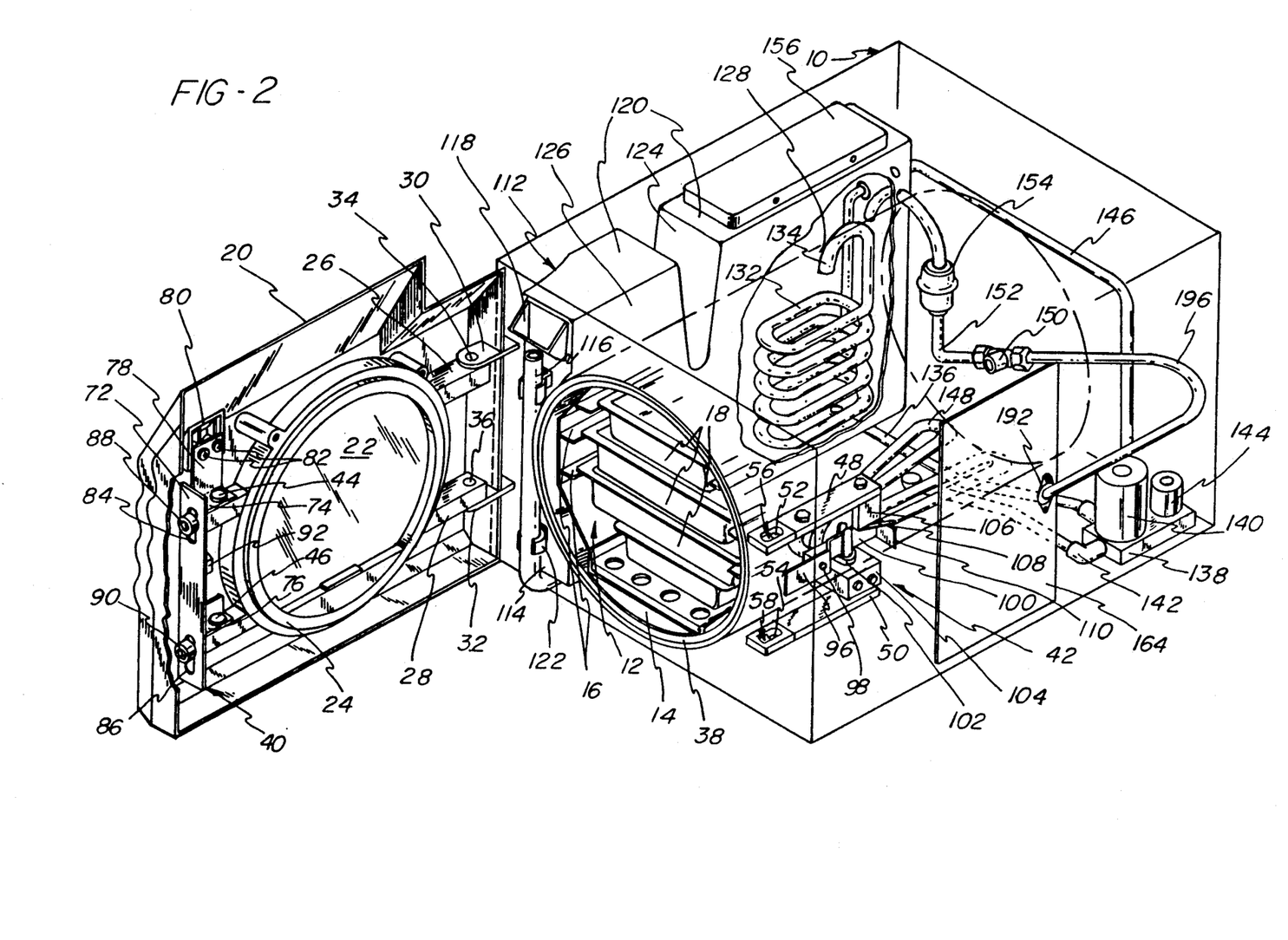
FIG. 2 is a partially cut-away perspective view of the sterilizer of the present invention with the door in a fully open position.

Referring to FIGS. 1 and 2, the sterilizer of the present invention includes an outer casing 10 within which a sterilizer chamber 12 is enclosed. The sterilizer chamber 12 includes means defining an opening 14 at a front portion of the sterilizer whereby articles may be placed inside the sterilizer chamber 12. As may be seen in FIG. 2, the sterilizer chamber 12 may be provided with support rails 16 for supporting article trays 18 within the chamber 12.

A door 20 defines a front portion of the sterilizer casing 10 and includes a chamber sealing plate 22 and an annular chamber seal 24 supported by the sealing plate 22. The sealing plate 22 is supported by upper and lower horizontal support bars 26, 28 which are mounted to shelf members 30, 32 by pivot pins 34, 36. Thus, the door 20 may be pivoted about a vertical axis toward and away from the chamber 12 whereby the seal 24 may contact a sealing surface 38 surrounding the chamber opening 14 to close and form an airtight seal around the opening 14, such that pressurized steam within the chamber 12 will be retained.

The upper and lower support bars 26, 28 carry latch means 40 at an end opposite from the pivot pins 34, 36 which cooperate with catch means 42 mounted in stationary relationship to the chamber 12. As may be best seen in FIGS. 2-4, the latch means 40 includes a pair of locking pins 44, 46 which extend through the upper and lower support bars 26, 28 to engage the catch means 42.

Figure 3:
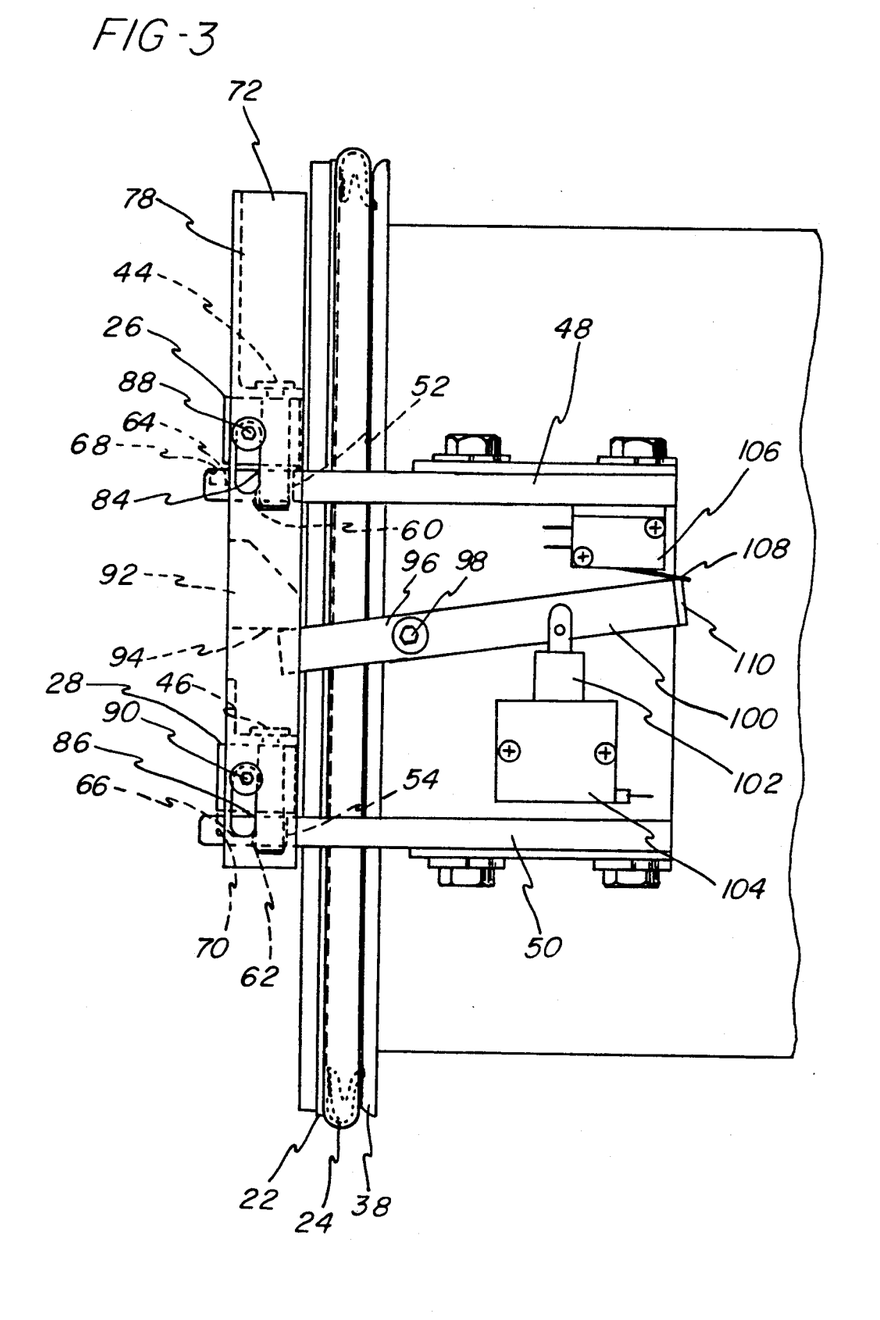
FIG. 3 is a side view of the latch mechanism for the door wherein the door is held in a fully closed position.
Figure 4:
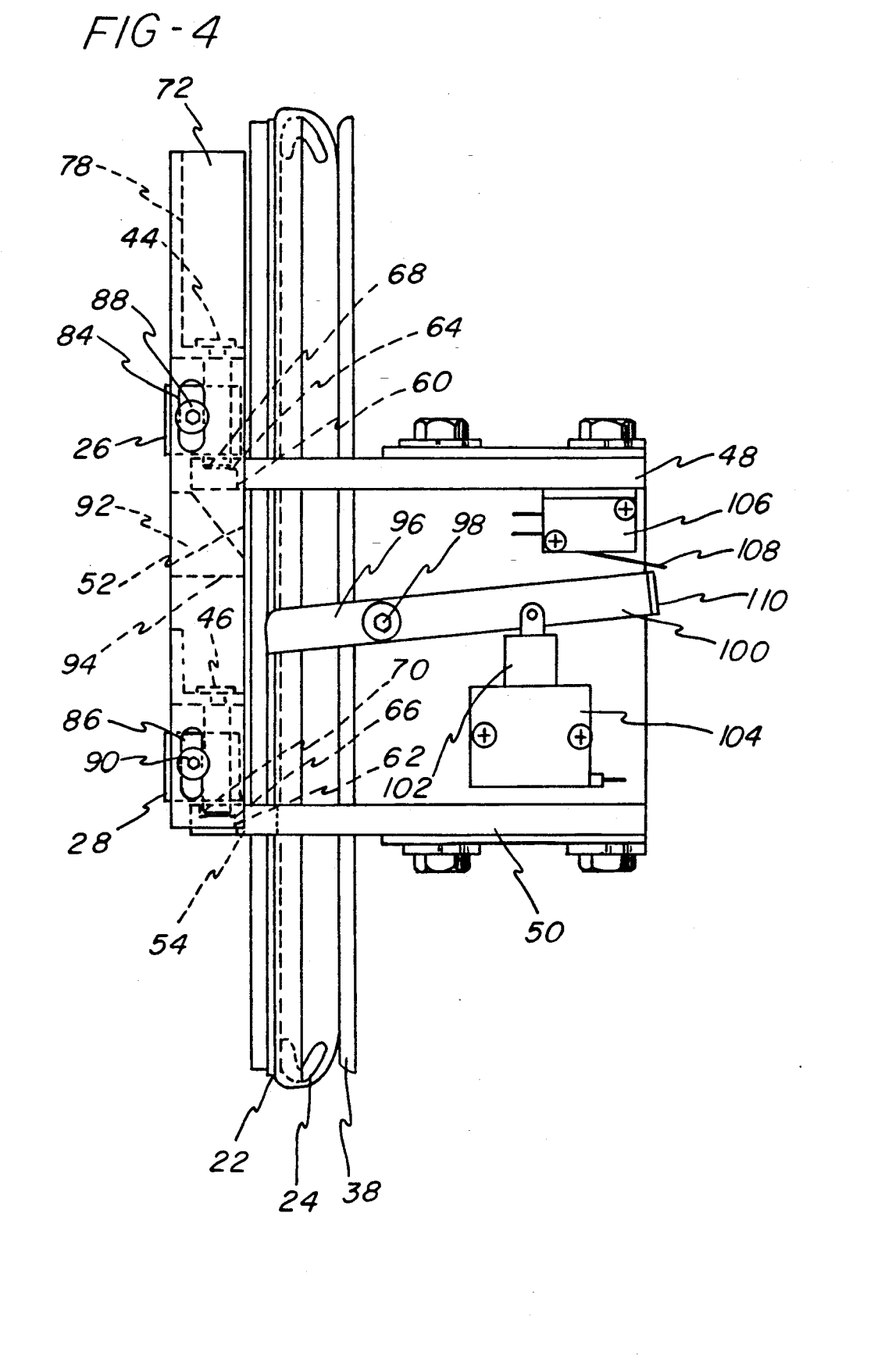
FIG. 4 is a side view of the latch mechanism for the door wherein the door is held in a partially open position.

The catch means 42 are defined by a pair of horizontally extending bars 48, 50 each of which includes a horizontal upper surface and apertures 52, 54 extending through the bars 48, 50, respectively, to form a first stop for the pins 44, 46 when the door 20 is in its closed position. The bars 48, 50 are further each provided with an elongated slot 56, 58 extending forwardly from the apertures 52, 54. A forward surface of each of the apertures 52, 54 adjacent to the slots 56, 58 form first stop surfaces 60, 62 for engaging a forwardly facing portion of each of the pins 44, 46 to prevent the door 20 from moving away from the chamber 12.

Each of the slots 56, 58 is defined by a horizontal pin supporting surface 64, 66 which is spaced vertically downwardly from the horizontal upper surface of the bars 48, 50, and a vertical second stop surface 68, 70 extending between the upper horizontal surface of the bars 48, 50 and the pin support surfaces 64, 66. The second stop surfaces 68, 70 face rearwardly toward the apertures 52, 54 to engage the pins 44, 46 after they are disengaged from the first stop surfaces 60, 62 to thereby hold the door in a partially open position spaced from the opening 14 of the chamber 12. In the preferred embodiment of the invention, the first and second stop surfaces are spaced from each other a distance which will limit the movement of the door 20 to less than one inch from the closed to the partially open position, and preferably a distance of approximately one-half inch.

The latch means 40 further includes a connecting member 72 extending vertically between the pins 44, 46 and pin carrier plates 74, 76 connecting the pins 44, 46 to the connecting member 72. The pin carrier plate 74 further includes a vertically extending handle attachment plate 78 which is attached to a handle 80 by appropriate fastener means 82.

The connecting member 72 is formed with a pair of vertically extending slots 84, 86 and a pair of bolts 88, 90 pass through the slots 84, 86 to engage the upper and lower support bars 26, 28, respectively, whereby the connecting member 72 is guided for vertical movement relative to the door 20. Thus, by lifting the handle 80 upwardly, the latch means 40 will be guided in vertical movement by the slots 84, 86 and bolts 88, 90 such that the pins 44, 46 will be moved vertically in an upward direction whereby they may be disengaged from the catch means 42. In addition, a latch bracket 92 is mounted to the connecting member 72 intermediate the horizontal support bars 26 and 28 and includes a downwardly facing horizontal surface 94.

Release means are provided in the form of a release bar 96 which is mounted by a pivot pin 98 between the bars 48, 50 and extends in substantially a front to rear direction. A forwardly located upper surface of the release bar 96 engages the horizontal surface 94 of the latch bracket 92 when the door 20 is in its closed position. A rearwardly located leg 100 of the release bar 96 is attached to a vertically movable plunger 102 which is actuated by solenoid 104 mounted in stationary relationship to the bars 48, 50, whereby the rear leg 100 of the release bar 96 may be moved downwardly to pivot the forward portion of the bar 96 in contact with the latch bracket 92 upwardly. Thus, the solenoid 104 may be actuated to cause the latch means 40 to move upwardly such that the pins 44, 46 are disengaged from the first stop surfaces 60, 62 and the door 20 is allowed to pivot outwardly until the pins 44, 46 contact the second stop surfaces 68, 70.

Referring to FIGS. 3 and 4, a switch 106 is mounted to a lower surface of the bar 48 and includes an actuation finger 108 extending downwardly therefrom. The rearward leg 100 of the release bar 96 includes a contact tab 110 extending below the finger 108 such that, when the door 20 is in its closed position, the surface 94 will rest upon the release bar 96 to cause the rearward leg 100 and tab 110 to pivot upwardly into contact with the finger 108 to cause contacts within the switch 106 to close. When the door 20 is moved away from its closed position, the plunger 102 in its rest position will permit the tab 110 to be located slightly below the finger 108 such that the contacts of the switch 106 will be open, as may be best seen in FIG. 4. The contacts of the switch 106 are electrically connected to control means for controlling the operation of the sterilizer as will be described further below.

A water reservoir 112 is located adjacent to the chamber 12 and extends in a front to rear direction along one side of the sterilizer. A front wall 114 of the water reservoir is located adjacent to the opening 14 of the chamber and includes a pair of clips 122 for mounting a flexible transparent tube 116 having an upper end which is open to the atmosphere and a lower end which opens into the bottom of the reservoir 112. Thus, the tube 116 forms a window through which the water level in the reservoir 112 may be viewed. Further, the tube 116 may be disengaged from the clips 122 and pivoted downwardly about its lower end to facilitate draining water from the reservoir 112. A fill spout 118 is also located on the front wall 114 adjacent to an upper wall 120 of the reservoir 112 for filling the reservoir 112. The tube 116 and fill spout 118 are positioned such that they are covered by a portion of the door 20 when the door 20 is closed.

The reservoir 112 includes a baffle portion 124 which separates the reservoir into front and rear portions wherein the front portion defines a water filling chamber 126 of the reservoir 112 and the rear portion forms a condensing cell 128 for receiving and condensing steam from the chamber 12. The baffle 124 extends from an uppermost portion of the reservoir at the upper wall 120 downwardly to a point below a predetermined minimum level for water in the reservoir 112. The predetermined water level may be defined by a water level sensor 130 located in a wall of the reservoir 112 (see FIG. 5). The sensor 130 preferably includes two exposed contacts which will conduct electricity when they are immersed below the water level in the reservoir 112.

Figure 5:
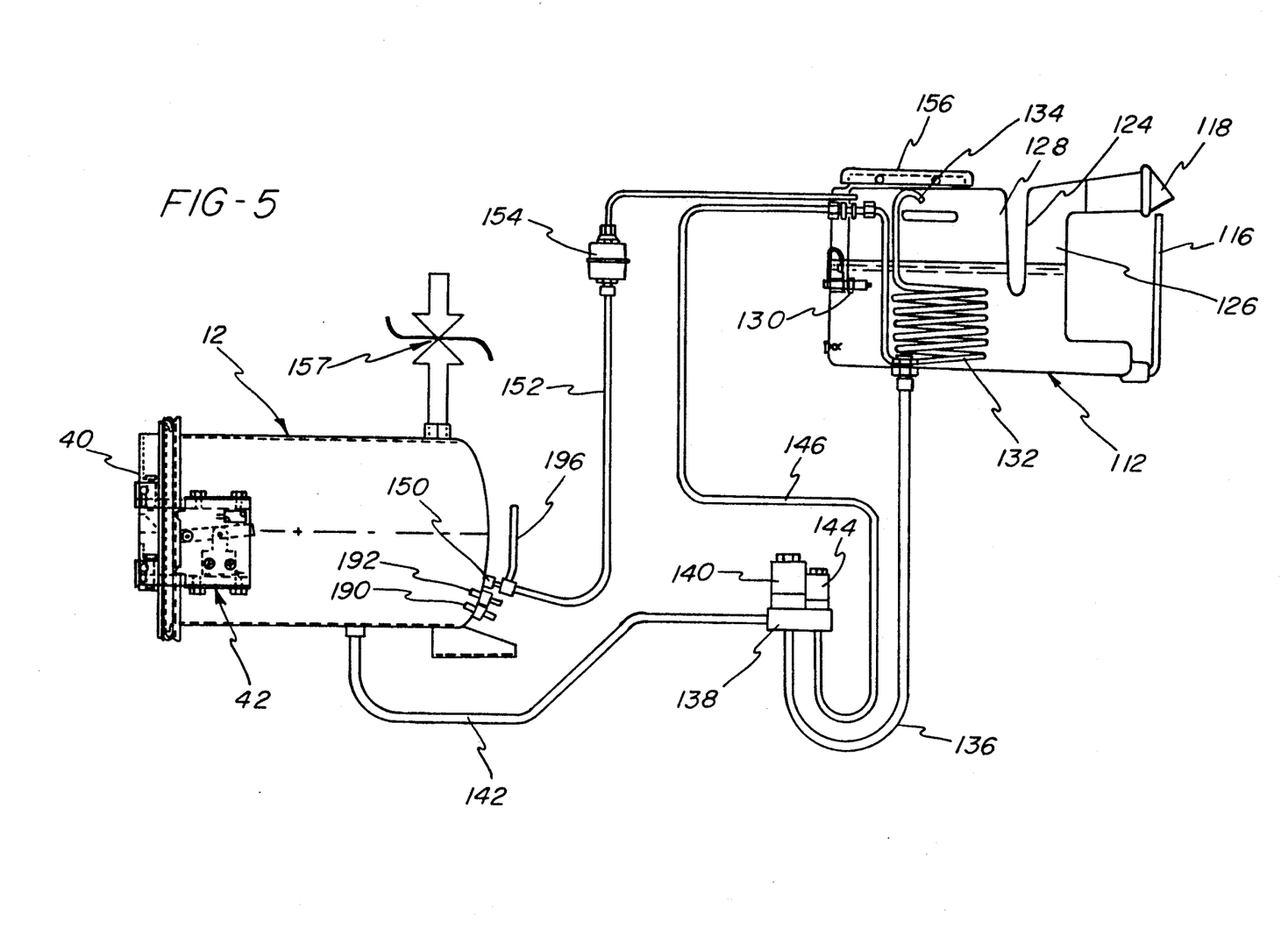
FIG. 5 is a diagrammatic view of the components for supplying steam to the chamber.

When the reservoir 112 is filled with water to a level at or above the water sensor 130, the baffle 124 and the water together form a vapor barrier such that any steam located in the condensing cell 128 will be prevented from flowing into the filling chamber 126 and out of the fill spout 118 and thus water in the sterilizer system is efficiently recovered.

A condensing coil 132 is positioned near the bottom of the condensing cell 128 and lies substantially below the level of the water level sensor 130. An inlet end of the coil 132 is located adjacent to a lower wall of the reservoir 112 and an exit end of the coil 132 is located at a point above the water sensor 130 such that the steam within the coil 132 travels upwardly as it is condensed and is discharged at a point above the water level of the reservoir 112.

Water is conveyed from the reservoir 112 to the chamber 12 by means of an outlet conduit 136 which carries the water to a solenoid controlled manifold 138. A first normally closed fill solenoid valve 140 may be opened to direct water from the conduit 136 into conduit 142 which enters the chamber 12 at a lower portion thereof, such that the chamber 12 may be filled with water from the reservoir 112.

The manifold 138 further includes a second normally closed vent solenoid valve 144 which may be actuated to connect the conduit 142 to a steam conduit 146 connected to the inlet of the coil 132. Thus, with solenoid valve 144 closed and solenoid valve 140 open, water may be transferred from the reservoir 112 to the chamber 12 and, with solenoid valve 140 closed and solenoid valve 144 open, steam may be transferred back from the chamber 12 to the reservoir 112 where it is condensed within the condensing cell 128.

A heating coil 148 is located in a lower portion of the chamber 12 and is supplied with power to heat the chamber 12 during a sterilization cycle. As the chamber 12 is heated by the heating coil 148, water located within the lower portion of the chamber will be evaporated to form steam and thereby facilitate transfer of heat to the articles located within the chamber 12 to be sterilized. An outlet 150 is positioned in a lower portion of the rear wall of the chamber 12 such that, as steam is formed and rises to the top portion of the chamber 12, any air in the chamber 12 will be displaced downwardly and exit through the opening 150. The air will pass from the opening 150 to an outlet pipe 152 having an outlet end which opens into the condensing cell 128 of the water reservoir 112. In addition, a conventional bellows valve 154 is located between the outlet 150 and the water reservoir 112 such that when the air and steam passing through the pipe 152 from the chamber 12 reaches a predetermined temperature, the valve 154 will close to stop the flow through the pipe 152 and thereby allow the pressure within the chamber 12 to increase.

In order to prevent a pressure build-up from occurring within the condensing cell portion 128 of the reservoir 112 as air and steam enters the reservoir 112 from the chamber 12, the reservoir 112 is provided with a venting cover 156 which is attached over an opening in the upper wall 120 of the condensing cell 128. The cover 156 is attached to the upper wall 120 by appropriate means such as staking so as to allow air to pass out of the chamber 128 while acting to prevent any steam located within the upper portion of the condensing cell 128 from exiting.

Further, to prevent an excessive pressure buildup from occurring within the chamber 12, a pressure relief valve 157 is provided i fluid communication with the chamber 12, as depicted schematically in FIG. 5.

Figure 6:
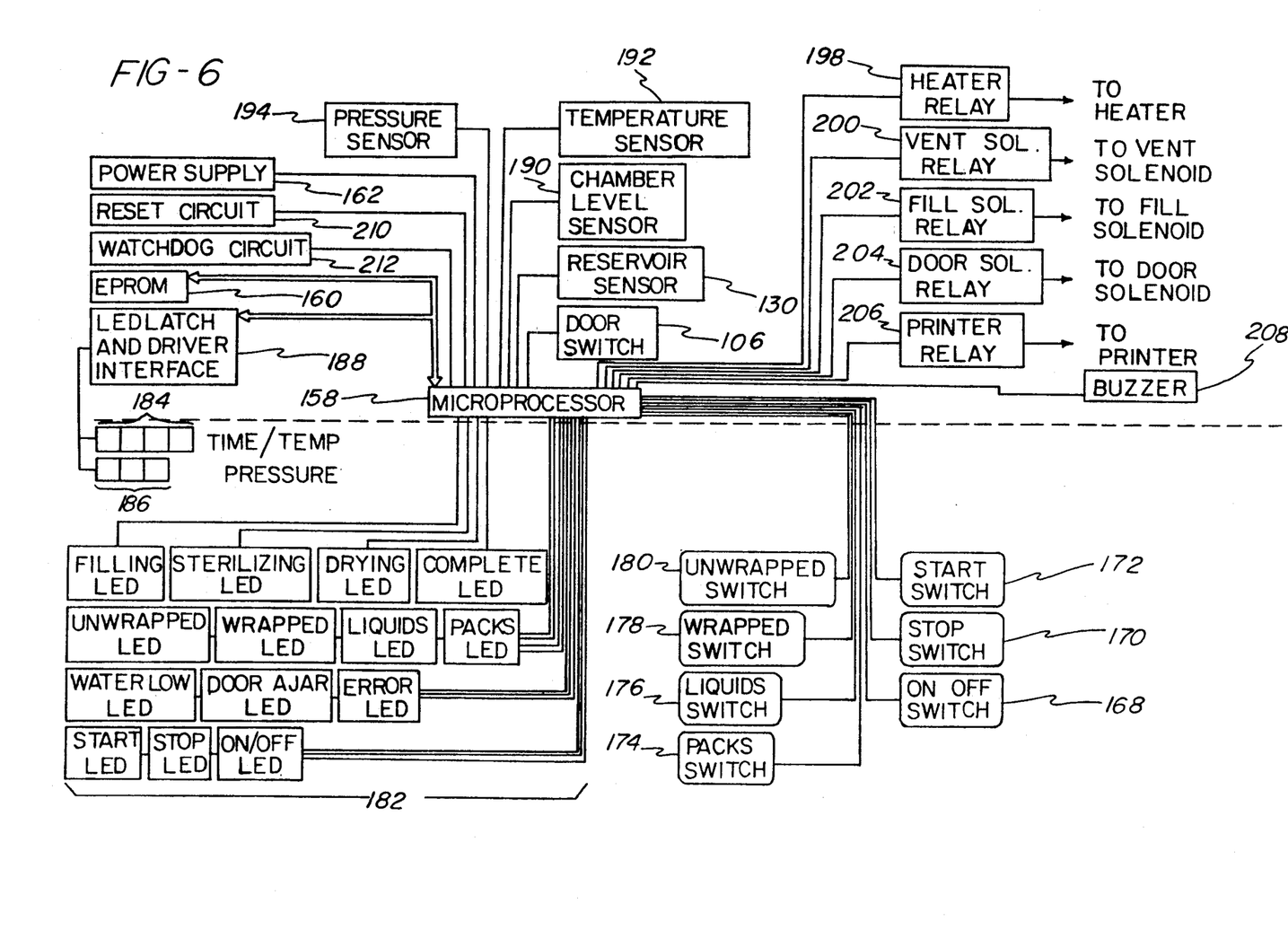
FIG. 6 is a schematic of the electrical components required to control the sterilization processes.

Control circuitry for the sterilizer is shown diagrammatically in FIG. 6 and includes a microprocessor 158 and an EPROM 160 which holds a program for controlling the operation of the microprocessor 158. In addition, a conventional power supply 162 is provided for supplying electrical power to the microprocessor 158 and various components associated therewith.

The microprocessor 158 is located on a main circuit board 164 located within the sterilizer and receives manually input signals from a display board 166 located on the front of the sterilizer. The display board 166 is provided with a set of buttons or contact switches 168 through 180 for turning the sterilizer on and off, for starting and stopping a sterilization cycle, and for selecting a particular sterilization cycle program.

In addition, a set of LED display lights 182 are connected to the microprocessor 158 to provide the operator of the sterilizer with information regarding the status of the various sterilizer operations and includes lights for indicating the particular sterilization cycle selected by the operator as well as warning lights to indicate that there is insufficient water in the water reservoir, that the door is not fully closed and to indicate that an interruption has occurred in the process of a sterilization cycle.

In the preferred embodiment, the operator may select from four different cycles which are to be regulated by the microprocessor 158 and includes a cycle for processing unwrapped articles which may be positioned directly within the sterilizer trays 18, a cycle for processing articles sealed within a wrapped package, a cycle for processing liquids and a cycle for processing articles which are grouped in a pack such as a tray containing the articles wrapped in a sealed manner by a cloth covering. The cycles differ from each other with regard to the temperature to which the sterilizer chamber 12 is heated and the amount of time the sterilizer remains at an elevated temperature.

The display panel 166 further includes a set of LEDs 184 for alternately displaying the temperature of the chamber 12 and a time output from the microprocessor 158 during a sterilization cycle, and another set of LEDs 186 to display the chamber pressure. The time/temperature and pressure LEDs 184, 186 are connected to the microprocessor 158 by a conventional LED latch and driver interface 188 such that the LEDs 184, 186 are adapted to display information which the microprocessor 158 has received and processed as it monitors the sterilization operation.

The microprocessor 158 receives input signals from the water level sensor 130 in the reservoir 112 and a water level sensor 190, similar to the sensor 130, located within the chamber 12, as well as from a temperature sensor 192 also located within the chamber 12. In addition, the microprocessor 158 is connected to the door switch 106 and to a chamber pressure sensor 194. The chamber pressure sensor 194 is preferably connected to the outlet 150 of the chamber 12 by an air line 196 and may be mounted on the main circuit board 164.

The water level sensors 130, 190 and the door switch 106 are essentially on/off switches which conduct a signal when the water is up to a certain predetermined level and when the door 20 is shut, respectively, and the temperature and pressure sensors 192, 194 provide a variable output which is directly proportional to the temperature and pressure within the chamber 12.

The microprocessor 158 further provides output signals to actuate relays for controlling the various operations of a sterilization cycle. The preferred embodiment of the present apparatus includes a heater relay 198 for controlling power to the heating coil 148, a vent solenoid relay 200 and fill solenoid relay 202 for controlling the power to the vent and fill solenoid valves 144, 140, respectively, a door solenoid relay 204 to control power to the door release actuating solenoid 104 and a printer relay 206 which may be used to control power to an optional printer (not shown) for printing a record of the sterilization cycle. The various relays may be electrically isolated from the microprocessor 158 by optocouplers (not shown) to protect the microprocessor 158 from damage which may result from the large current requirements of the relays.

Further, a buzzer 208 is provided for audibly signaling the operator during a sterilization cycle and actuation of the buzzer 208 is programmed to occur at certain predetermined stages of each of the sterilization cycles.

Additional circuits, labeled as reset and watchdog circuits 210 and 212, respectively, are provided for preventing noise in the power supply line from causing the microprocessor 158 to "lock up" while it is running a program, and for monitoring an output from the microprocessor 158 indicating that an interruption in the operation of the microprocessor 158 has occurred such that a reset must be initiated, i.e., the sterilization cycle must be restarted from the beginning of the program.

Figure 7A:
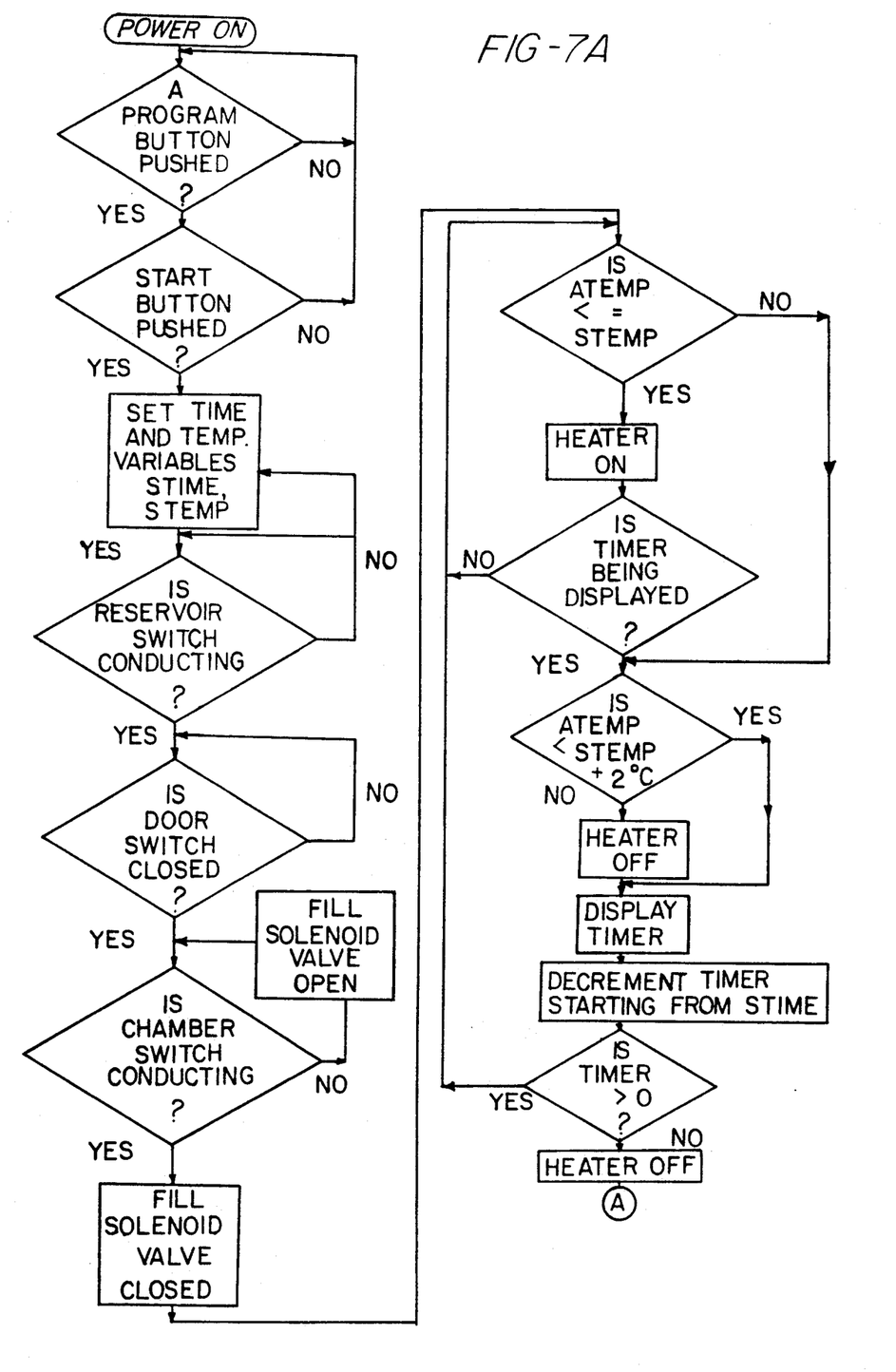
FIGS. 7A-7C show a flow chart depicting the operation of the sterilizer during a sterilization process.
Figure 7B:
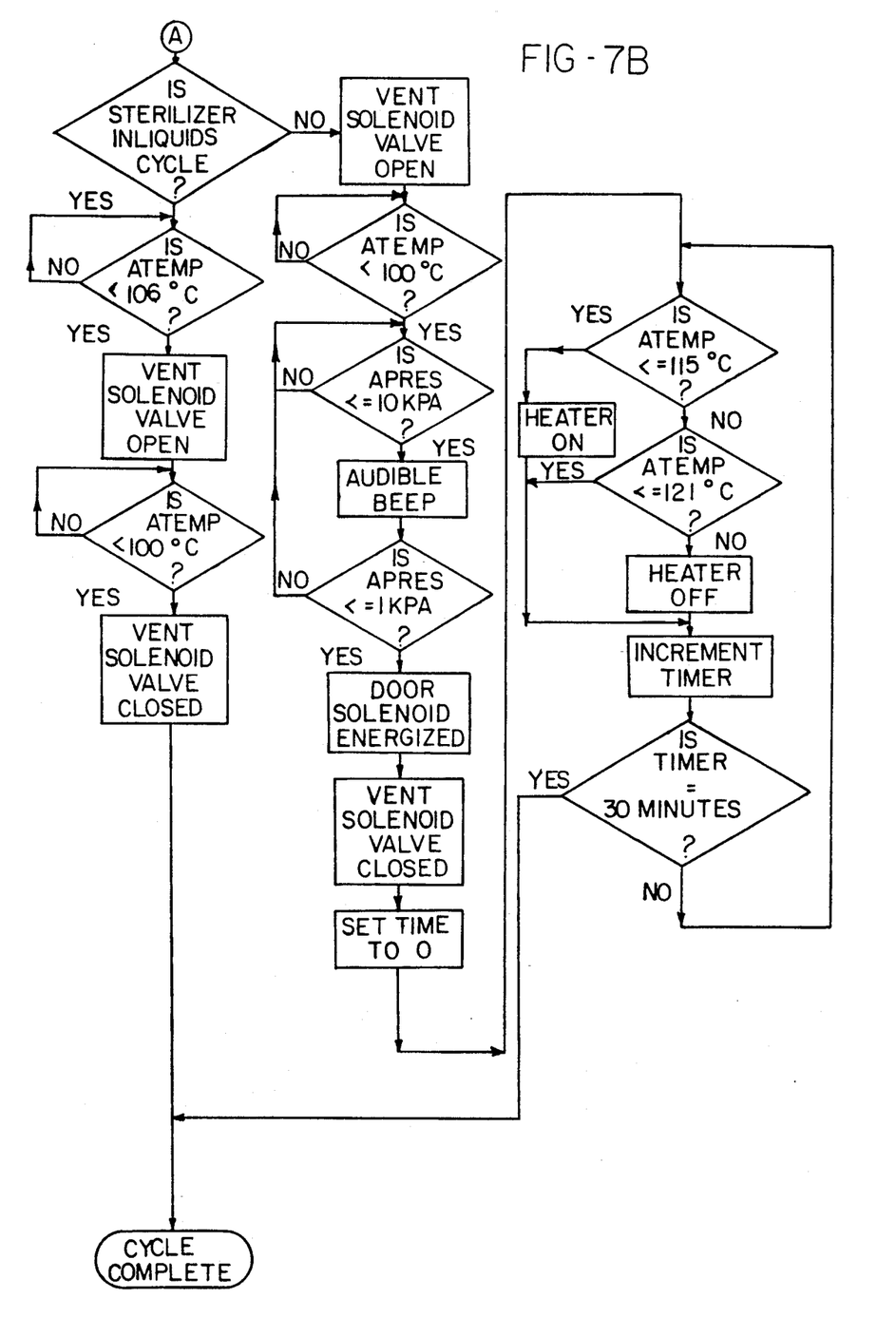

Referring now to the flow chart shown in FIGS. 7A and 7B, the operation of the sterilizer during a typical sterilization cycle for non-liquid articles will be described. Initially, after articles to be sterilized have been placed within the chamber 12 and the operator has pushed the on/off switch 168 to turn the sterilizer on, the normally closed fill and vent solenoid valves 140, 144 will remain closed while the microprocessor scans the program selection switches 174 through 180 to determine whether a sterilization cycle has been selected.

After a program switch has been pushed, the microprocessor 158 continues to scan the program selection switches 174-180 until the start switch 172 is pushed to initiate the cycle. At the initiation of the cycle, a set time and set temperature corresponding to the sterilization time and sterilization temperature is loaded into the microprocessor 158 for future reference during the sterilization cycle and is displayed on the display panel 166. The microprocessor 158 then checks to see that the reservoir switch 130 is conducting thus indicating that the water in the reservoir 112 is at an acceptable level. If the water in the reservoir 112 is low, an LED on the display panel 166 will light up to indicate this condition and the buzzer will be activated to beep until the reservoir is filled with water. After the reservoir 112 has sufficient water, the microprocessor 158 will then check to see that the door switch 106 is closed, as indicated by the position of the actuation finger 108 shown in FIG. 3. If the door 20 is ajar, an indicator LED will light up on the panel 166 and the buzzer 208 will sound until the door 20 is moved to its fully closed position.

The fill solenoid valve 140 will then be opened to permit water to flow from the reservoir 112 to the chamber 12. The microprocessor 158 will monitor the chamber switch 190 to determine when the water level in the chamber 12 reaches the level of the switch 190, at which time the power to the fill solenoid valve 140 will be shut off to close the valve. In addition, an LED will light up on the display panel as the chamber 12 is being filled to indicate to the operator that the sterilizer is undergoing the filling phase of the cycle.

When the chamber 12 has been filled to the desired level with water, the filling LED will be shut off and a sterilizing LED will come on to indicate that the sterilizer is beginning the heated sterilizing cycle. During this portion of the cycle, power will be supplied to the heating coil 148 and the actual temperature, designated ATEMP, will be compared to the set temperature, designated STEMP. If the actual temperature is less than or equal to the set temperature, power will continue to be supplied to the heater. When the temperature within the chamber 12 exceeds the set temperature, the microprocessor 158 will check to see whether the actual temperature is also less than the set temperature plus 2° C., in which case power will continue to be supplied to the heater and a time reading will be sent to the display panel 166 initially corresponding to the set time for the particular cycle selected. The microprocessor 158 will then check to see whether the timer value is greater than zero thus indicating that the sterilization cycle is not completed and, if the timer value is greater than zero, the program will return to the point where it checks to see whether the actual temperature is less than or equal to the set temperature.

The microprocessor 158 will continue to cycle through this portion of the program decrementing the timer for each pass through the temperature checking loop while maintaining the temperature between the set temperature and a temperature equal to the set temperature plus 2° C. When the timer has been decremented to zero, the sterilizing LED will be shut off and the power to the heater will be terminated. At this point in the program the microprocessor 158 will check to see whether the operator has selected a liquid cycle or a non-liquid cycle, i.e., a cycle for packs, wrapped or unwrapped articles.

If the sterilizer is in a non-liquid cycle, the vent solenoid valve 144 will be opened to allow steam to pass through the lines 142, 146 to be condensed by the coil 132 located in the condensing cell 128 of the water reservoir 112. The microprocessor 158 will continue to monitor the chamber temperature until the temperature falls below 100° C. at which time the microprocessor 158 will monitor the pressure. The buzzer will be activated to sound an audible beep when the pressure is equal to or less than 10 kpa and will continue to sound an alarm to indicate that the chamber pressure is approaching a level which will permit the door to be opened. When a pressure of 1 kpa or less is sensed, the door solenoid 104 will be energized to pull the leg 100 of the release bar 96 downwardly whereby the latch bracket 92 will be moved upwardly to move the locking pins 44, 46 out of contact with the first stop surfaces 60, 62 and allow the small remaining pressure within the chamber 12 to cause the door 20 to pivot outwardly such that the pins rest against the second stop surfaces 68, 70, as depicted in FIG. 4.

When the door is opened, the power to the vent solenoid valve 144 will be terminated to close the valve and a timer within the microprocessor 158 will be set to zero in preparation for timing a drying portion of the cycle. During the drying portion of the cycle, the microprocessor 158 actuates the heater control relay 198 to provide power to the heater 148 such that the temperature within the chamber 12 is maintained between 115° C. and 121° C. The drying portion of the sterilization cycle lasts for 30 minutes, during which time an LED is caused to light up on the display panel 166 to notify the operator that the sterilizer is in the drying stage of the cycle. At the termination of the drying step, the drying LED will be turned off, an LED to indicate that the sterilization cycle is complete will be turned on and the buzzer will be activated to audibly alert the operator that the articles may be removed from the sterilizer.

Figure 7C:
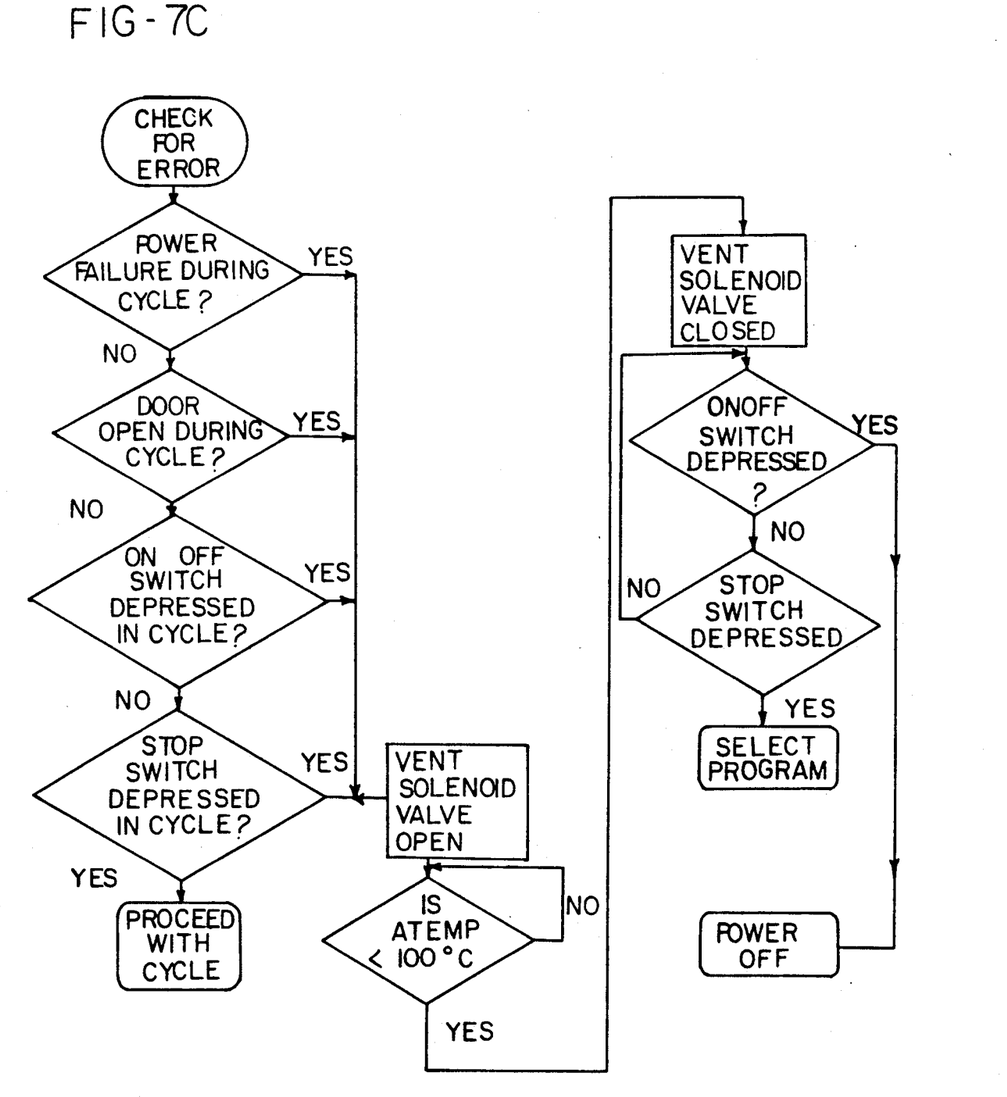

FIG. 7C shows a program followed by the watchdog circuit 212 throughout the sterilization cycle. The watchdog circuit 212 monitors an output from the microprocessor 158 to determine whether any error condition or interruption has occurred which would effect the proper sterilization of the articles within the chamber 12 and includes a check for power failure, opening of the door during the cycle, actuation of the on/off switch during the cycle and actuation of the stop switch during the cycle. If none of the above conditions occurs, the watchdog circuit 212 permits the microprocessor 158 to continue with the sterilization cycle. However, if any of the error conditions occurs, the heater 148 is turned off, the vent solenoid valve 144 is caused to open to release the pressure within the chamber 12, an error LED is caused to flash on the display panel 166, the buzzer 208 is caused to sound an audible beeping alarm and the temperature within the chamber 12 is monitored until it drops below 100° C. at which time the vent solenoid 144 is closed. At this point, the operator has the option of either turning the sterilizer off or actuating the stop switch which will terminate the error signal and the audible alarm and bring the program back to a point where the operator may again select the program for the sterilization cycle.

If a liquids cycle has been selected, the sterilization program will not include a drying step but rather, the vent solenoid valve 144 will be maintained in a closed position at the end of the cycle until the temperature within the chamber 12 drops below 106° C. with the chamber door closed and the heater turned off. When the temperature has dropped below 106° C., the vent solenoid valve 144 will be opened and the temperature will be allowed to drop further until it is below 100° C. At this time the vent solenoid valve 144 will be closed in preparation for another sterilization cycle and the buzzer 208 will signal the operator that the door 20 may be opened to remove the sterilized liquids. By permitting the sterilizer to cool down gradually with the door closed, the increased pressure within the sterilizer is allowed to decrease gradually along with the temperature such that the liquids will not boil, as would be the case if the vent solenoid valve 144 were opened while the chamber 12 and the liquids contained therein were still at an elevated temperature.

It should be noted that the present door latching mechanism is designed such that a high degree of force is required to move the pins 44, 46 upwardly out of contact with the first stop surfaces 60, 62 when the pressure within the chamber is greater than 1 kpa. The force for holding the latch pins 44, 46 in place results from the high frictional forces produced between the pins 44, 46 and the first stop surfaces 60, 62 as the pressure within the chamber 12 exerts an outward pressure on the door 20. Thus, the operator will be prevented from inadvertently opening the door 20 while the sterilizer chamber 12 is still at an elevated pressure.

While the form of apparatus herein described constitutes a preferred embodiment of the invention, it is to be understood that the invention is not limited to this precise form of apparatus and that changes may be made therein without departing from the scope of the invention which is defined in the appended claims.

What is claimed is:

1. A sterilizing apparatus in which articles can be sterilized in a steam environment at preselected temperatures, said apparatus comprising:
   a sterilizing chamber having means defining an opening in said chamber;
   a door mounted for movement relative to said chamber between a closed position wherein said door is in sealing contact with said chamber opening and a fully open position wherein articles may be inserted into said chamber;
   control means for controlling a sterilization process; and
   latch and catch means mounted to said door and said chamber for movement relative to each other; said latch means cooperating with a first surface on said catch means to hold said door in a first stop position with said door in sealing contact with said chamber opening and said latch means cooperating with said catch means to hold said door in a second stop position spaced from said chamber opening and intermediate said fully open and closed positions of said door wherein said latch means engages a second surface on said catch means to prevent said door from moving to said fully open positions wherein said control means causes said door to be automatically released from said first stop position to said second stop position at the conclusion of said sterilization process.

2. The apparatus of claim 1 wherein said latch means includes a pin and said catch means include means defining an aperture for receiving said pin.

3. The apparatus of claim 2 wherein said aperture defines said first surface for contacting said pin in said first stop position and said catch means defines said second surface spaced from said first surface for contacting said pin in said second stop position.

4. The apparatus of claim 1 including release means for causing said latch means to move relative to said catch means whereby said latch means said door move from said first to said second stop position.

5. The apparatus of claim 4 wherein said control means automatically actuates said release means at the conclusion of said sterilization process.

6. The apparatus of claim 4 including a switch having contacts which are actuated by said release means to send a signal to said control means when said door is open.

7. The apparatus of claim 4 wherein said release means includes an elongated bar mounted for pivotal movement relative to said catch means, said bar including an end for contacting said latch means.

8. The apparatus of claim 7 including solenoid means for moving an end of said bar opposite from said latch means, said solenoid means being actuated by said control means.

9. The apparatus of claim 8 including means for sensing the pressure within said chamber, said control means being adapted to actuate said solenoid means upon sensing a pressure which is less than a predetermined pressure.

10. The apparatus of claim 1 including a water reservoir and means for supplying water to said sterilizing chamber from said reservoir.

11. The apparatus of claim 10 including means for filling said water reservoir and means for receiving steam into said reservoir from said sterilizing chamber and a baffle element extending downwardly from an uppermost portion of said reservoir to form a vapor barrier between said means for filling and said means for receiving steam when said reservoir is filled with water to a level where said water contacts said baffle element.

12. The apparatus of claim 10 including solenoid actuated vent and fill valves connected to said control means to control flow of stream from said chamber to said water reservoir and flow of water from said reservoir to said chamber, respectively.

13. The apparatus of claim 12 wherein said control means is adapted to terminate said sterilization process and open said vent valve when said door is opened during sterilizer operation.

14. A sterilizing apparatus in which articles can be sterilized in a steam environment at preselected temperatures, said apparatus comprising:
   a sterilizing chamber having means defining an opening in said chamber;
   a door mounted for engagement with said means defining said chamber opening whereby said door forms an airtight seal over said chamber opening when so engaged, said door being movable away from said opening;
   means for holding said door in engagement with said means defining said chamber opening during a sterilization process, wherein said means for holding said door includes latch and catch means, said latch means being mounted to said door and said catch means being mounted to said chamber and including first and second stop means, said latch means engaging said first stop means to hold said door in engagement with said means defining said opening in said chamber and said latch means engaging said second stop means to limit the opening of said door upon release of said latch means from said first stop means;

means for supplying said chamber with steam including a reservoir for containing water, said reservoir having a baffle separating said reservoir into a front portion and a rear portion, said front portion including a fill spout for filling said reservoir with water and said rear portion forming a condensing cell for receiving and condensing steam from said chamber;

control means for controlling a sterilization process, and release means for releasing said latch means from said first stop means and for causing said means for holding said door to release said door from said chamber opening in response to a signal from said control means at the termination of a sterilization process whereby said door moves away from said chamber opening and gas within said chamber is expelled.

15. The apparatus of claim 14 wherein said door is caused to move away from said chamber opening by means of gas pressure within said chamber exerting a force on said door upon said door being released by said release means.

16. The apparatus of claim 14 wherein said door moves a distance of less than one inch from said first stop means to said second stop means.

17. The apparatus of claim 14 wherein said release means includes a solenoid actuated mechanism which engages said latch means to release said door from said chamber.

18. The apparatus of claim 17 further including a door handle connected to said latch means wherein said door handle is moveable relative to said door to cause said latch means to release said door for movement away from said chamber.

19. The apparatus of claim 14 including pressure sensing means, said control means causing actuation of said release means when the pressure in said chamber falls below a predetermined pressure.

20. The apparatus of claim 19 wherein said predetermined pressure is approximately 1 kpa.

21. The apparatus of claim 14 wherein said reservoir for containing water includes a front end adjacent to said opening in said chamber and a window mounted to said front end whereby the water level in said reservoir may be viewed.

22. The apparatus of claim 21 including a pipe for conveying water from said reservoir to said chamber, heating means for heating water in said chamber to form steam, an evacuation pipe for conveying air from said chamber to said reservoir as steam fills said chamber, and a cut-off valve for closing said evacuation pipe, said cut-off valve operating in response to an increase in temperature of gas being conveyed through said evacuation pipe.

23. The apparatus of claim 21 wherein water is conveyed from said reservoir to said chamber and sensing means are provided within said chamber for sending a signal to said control means when the water reaches a predetermined level within said chamber.

24. The apparatus of claim 21 wherein said said baffle extends downwardly into said reservoir such that a vapor barrier is formed by said baffle between said front and rear portions to thereby prevent steam from exiting said reservoir through said front portion when said reservoir is filled with water to a level where said water contacts said baffle.

25. The apparatus of claim 24 including coil means located in said rear portion of said reservoir for receiving steam from said chamber wherein said coil means is immersed in water in said reservoir when said reservoir is filled with water to a level where said water contacts said baffle and steam enters said coil means at a point adjacent to a bottom portion of said reservoir and travels through said coil to a point adjacent to a top portion of said reservoir and is discharged from said coil.

26. The apparatus of claim 24 wherein a portion of said door is positioned over said window and said fill spout when said door is engaged over said chamber opening and exposes said window and fill spout for access when said door is moved away from said chamber.

* * * * *

UNITED STATES PATENT AND TRADEMARK OFFICE
CERTIFICATE OF CORRECTION

PATENT NO. : 5,223,229
DATED : June 29, 1993
INVENTOR(S) : Jeffrey P. Brucker

It is certified that error appears in the above-identified patent and that said Letters Patent is hereby corrected as shown below:

Column 11, line 59, "positions" should be --position--.

Column 12, line 6, after "means", second occurrence, the word "and" has been omitted; line 41, "stream" should be --steam--.

Signed and Sealed this

Fifteenth Day of February, 1994

Attest:

BRUCE LEHMAN

Attesting Officer   Commissioner of Patents and Trademarks